(12) United States Patent
Freehill et al.

(10) Patent No.: US 6,718,816 B2
(45) Date of Patent: Apr. 13, 2004

(54) MONOLITHIC I.C. IMPLEMENTED CALIBRATION CIRCUIT

(75) Inventors: Thomas A. Freehill, Bozrah, CT (US); Timothy B. Straw, Narragansett, RI (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 0 days.

(21) Appl. No.: 10/390,696

(22) Filed: Mar. 19, 2003

(65) Prior Publication Data

US 2003/0177810 A1 Sep. 25, 2003

Related U.S. Application Data

(62) Division of application No. 09/932,565, filed on Aug. 13, 2001, now Pat. No. 6,571,598.

(51) Int. Cl.⁷ .............................................. G01D 18/00
(52) U.S. Cl. ........................................ 73/1.01; 73/1.83
(58) Field of Search .................................. 73/1.01, 1.83; 324/601; 330/2; 367/13

(56) References Cited

U.S. PATENT DOCUMENTS

| | | | | |
|---|---|---|---|---|
| 3,591,854 A | * | 7/1971 | Cole .............................. | 327/7 |
| 3,774,052 A | * | 11/1973 | McClain ....................... | 327/74 |
| 4,689,578 A | * | 8/1987 | Spychalski .................... | 330/2 |
| 6,011,433 A | * | 1/2000 | Nairn ............................ | 330/2 |
| 6,242,974 B1 | * | 6/2001 | Kunst ............................ | 330/9 |
| 6,424,209 B1 | * | 7/2002 | Gorecki et al. ............. | 327/554 |
| 2003/0090300 A1 | * | 5/2003 | Nix .............................. | 327/77 |

* cited by examiner

*Primary Examiner*—Hezron Williams
*Assistant Examiner*—Charles D Garber
(74) *Attorney, Agent, or Firm*—James M. Kasischke; Michael F. Oglo; Jean-Paul A. Nasser

(57) ABSTRACT

The calibration circuit is used with a differential input, monolithic integrated circuit preamplifier in a sensor system. The calibration circuit tests the integrity of the sensor, the preamplifier, and the wiring in the sensor system. The calibration circuit includes first and second calibration capacitors having different capacitances connected to the preamplifier input leads. A calibration signal source is connected between the capacitors. The capacitors are preferably implemented on the same integrated circuit as the preamplifier. In operation, a calibration signal of known amplitude is applied to the calibration circuit and the level at the preamplifier output is determined. The level at the preamplifier output indicates certain conditions relating to the integrity of the sensor and its wiring, for example, an open circuit condition or a short circuit condition.

3 Claims, 3 Drawing Sheets

MONOLITHIC I.C. IMPLEMENTED CALIBRATION CIRCUIT

CROSS REFERENCE TO OTHER PATENT APPLICATIONS

This application is a division of the patent application Ser. No. 09/932,565, filed Aug. 13, 2001 and now U.S. Pat. No. 6,571,598.

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION (1) Field of the Invention

The present invention relates to the calibration of preamplifiers and more particularly, to a calibration circuit for use with a differential input, monolithic integrated circuit preamplifier.

(2) Description of the Prior Art

A preamplifier is commonly used with a sensor, such as a hydrophone, to amplify low level signals received from the sensor. Such preamplifiers can be constructed in a single monolithic integrated circuit in small sizes. The small size of such preamplifiers allows placement close to the sensor without adversely affecting the sensor's performance. One such preamplifier is disclosed in U.S. Pat. No. 5,339,285, incorporated herein by reference.

A calibration circuit can be used with the sensor and preamplifier to test the integrity of the sensor and preamplifier. One method for calibrating a differential input amplifier involves injecting a single ended signal at a point past the input stage of the amplifier. One problem with this method is that the input stage, the sensor, and the interconnect wiring are not tested. According to another method, a differential signal is injected at the inputs to the amplifier. Although this method is capable of testing all circuitry, this method has required complicated wiring schemes and switching to prevent both unwanted noise coupling via the calibration circuitry and an impedance imbalance that would degrade the amplifier's common mode rejection.

Another method of calibration is disclosed in U.S. Pat. No. 4,648,078. This patent, however, discloses calibration of a single ended preamplifier, not a differential preamplifier.

SUMMARY OF THE INVENTION

Accordingly, one object of the present invention is to calibrate a preamplifier as well as its associated sensor and interconnect wiring without requiring overly complicated wiring schemes and switching.

Another object of the present invention is to provide calibration circuitry for a differential input, monolithic integrated circuit preamplifier, which can easily be implemented on a single integrated circuit.

The present invention features a calibration circuit for a differential input preamplifier having first and second preamplifier inputs. The calibration circuit comprises first and second capacitors connected to respective first and second preamplifier inputs. The first and second capacitors have different capacitance values. A calibration signal source is connected between the first and second capacitors for applying a calibration signal.

The present invention also features a calibrated preamplifier for use with a sensor. The calibrated preamplifier comprises a differential input, single-ended output amplifier and a calibration circuit connected across first and second inputs of the amplifier. The calibration circuit applies a calibration signal to create a difference voltage between the inputs.

In one preferred embodiment, the amplifier and the calibration circuit are implemented on a monolithic integrated circuit. In one embodiment, only the calibration capacitors are implemented on the monolithic integrated circuit. In another embodiment, the calibration capacitors and the calibration signal source are both implemented on the monolithic integrated circuit.

The present invention also features a sensor system comprising a sensor having first and second output leads and a differential input, single ended output amplifier having first and second input leads connected to the first and second output leads of the sensor. A calibration circuit is connected across the first and second output leads of the sensor and the first and second input leads of the differential input single ended output amplifier. The calibration circuit applies a calibration signal to create a difference voltage between the amplifier input leads such that the preamplifier output voltage indicates the presence or absence of sensor impedance.

The preamplifier preferably includes first and second input resistors connected across the first and second input leads to form an analog filter with the sensor capacitance. The capacitance values of the first and second capacitors are preferably less than the capacitance of the sensor. In one embodiment, the sensor is a hydrophone. In another embodiment, the sensor is an accelerometer.

BRIEF DESCRIPTION OF THE DRAWINGS

These and other features and advantages of the present invention will be better understood in view of the following description of the invention taken together with the drawings wherein.

DESCRIPTION OF THE PREFERRED EMBODIMENT

Figure 1:
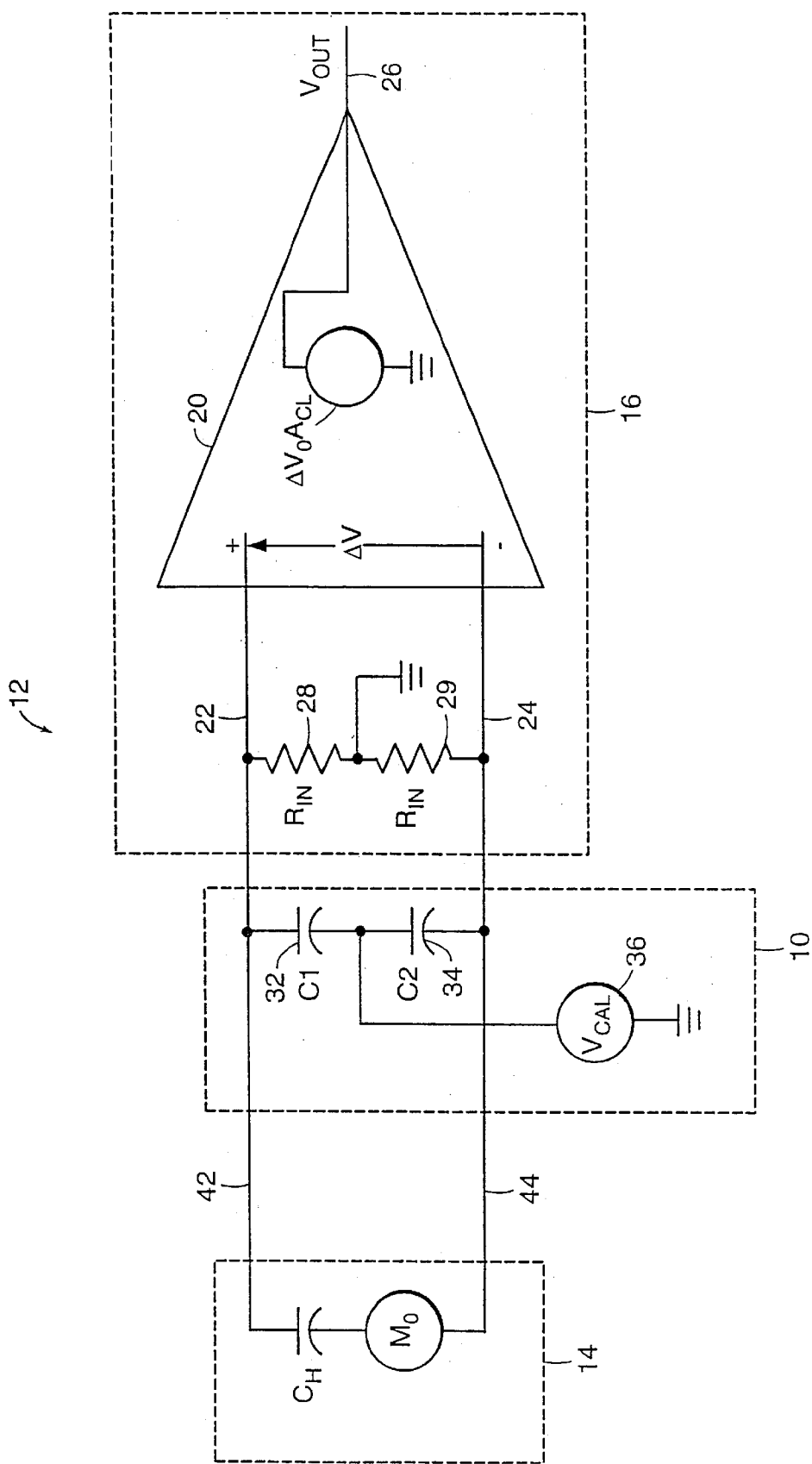
FIG. 1 is a circuit diagram of a sensor system including the calibration circuit, according to the present invention.

The calibration circuit 10, FIG. 1, according to the present invention, is used in a sensor system 12 including a sensor 14 and a preamplifier 16 connected by wiring 22, 24, 42, 44. The calibration circuit 10 is used to test the integrity of the preamplifier 16 as well as the associated sensor 14 and interconnect wiring 22, 24, 42, 44. In one example, the sensor 14 is a hydrophone, but the calibration circuit 10 of the present invention can also be used with other types of sensors such as accelerometers.

The preamplifier 16 is preferably a differential input preamplifier. The preamplifier 16 preferably includes a differential input, single ended output amplifier 20 having first and second input leads 22, 24 and lead 26 carrying an output signal. The first and second amplifier input leads 22, 24 are connected to respective first and second sensor output leads 42, 44. First and second input resistors 28, 29 of equal values, $R_{IN}$, are preferably connected to the first and second amplifier inputs 22, 24. The differential input arrangement may take the form well known in art shown in the drawing. Resistors 28 and 29 have one of their respective ends connected to respective input leads 22 and 24, with the other ends of the resistors grounded. The output of amplifier 26 is a potential relative to ground. The input resistors 28, 29 form an analog filter with the sensor capacitance but do not affect the operation of the calibration circuit 10 at normal operating frequencies. The voltage difference between the preamplifier input leads 22, 24 is represented by ΔV, the amplifier closed loop voltage gain is represented by $A_{CL}$, and the preamplifier output voltage $V_{OUT}$ is equal to the product of $A_{CL}$ and ΔV.

The calibration circuit 10 consists of first and second calibration capacitors 32, 34 and a calibration signal source 36. The calibration capacitors 32, 34 are connected to the sensor output leads 42, 44 and to the preamplifier input leads 22, 24, respectively. Note that in the embodiment of differentially inputted sensor preamplifier shown, both the junction between calibration capacitors 32, 34 and the junction between the preamplifier resistors 28, 29 are grounded. The calibration capacitors 32, 34 are preferably implemented on the same integrated circuit as the preamplifier 16. The calibration signal source 36 can be located on the same integrated circuit or external to the integrated circuit containing the preamplifier 16. Where the calibration voltage source 36 is included on the integrated circuit, external circuitry requirements are eliminated from the system except for a single control line to enable/disable the calibration circuitry.

The capacitance ($C_1$ and $C_2$) of the calibration capacitors 32, 34 and the sensor capacitance ($C_H$) together form an attenuator that can be used to measure the characteristics of the sensor 14 and its wiring 42, 44. The amount of attenuation is inversely proportional to the ratio of the capacitance ($C_1$ and $C_2$) of each of the calibration capacitors to the hydrophone capacitance ($C_H$). The capacitors 32, 34 each form a voltage divider with a component of the sensor capacitance $C_H$. When a calibration signal is present, the combination of the three capacitances ($C_H$, $C_1$ and $C_2$) develops specific voltages at each of the preamplifier inputs 22, 24. The preamplifier 16 generates an output signal proportional to the difference of the two preamplifier inputs 22, 24. Thus, the capacitance values $C_1$, $C_2$ of the capacitors 32, 34 are preferably not equal such that a difference in voltage exists between the two preamplifier input leads 22, 24 and the net preamplifier output is not zero. In other words, a differential signal at the preamplifier input leads 22, 24 results in a signal at the preamplifier output 26.

The value of the differential voltage at the preamplifier input leads and the attenuation of the calibration signal $V_{CAL}$ can be calculated according to the following equations:

$$\Delta V = V_{CAL} \left[ \frac{2C_H(C_1 - C_2)}{2C_H(2C_H + C_1 + C_2) + C_1 \cdot C_2} \right] \quad (1)$$

$$\text{Attenuation} = 20 \ \log\left[ \frac{2C_H(C_1 - C_2)}{2C_H(2C_H + C_1 + C_2) + C_1 \cdot C_2} \right] Db \quad (2)$$

The capacitance values ($C_1$ and $C_2$) of the calibration capacitors 32, 34 are preferably much less than the capacitance value $C_H$ of the sensor 14 plus any stray capacitance, for example, from cabling, preamplifier input capacitance, and the like. This ensures that the calibration circuit 10 has minimal affect upon loading the sensor 14, and has minimal effect upon the common mode rejection of the preamplifier 16. Also, the frequency range of interest is preferably greater than two times the highest pole formed by either the first or second capacitor 32, 34 and the total input resistance of the preamplifier 16 (i.e., the high frequency pole formed by resistors 28 and 29 and the smaller of the capacitors 32, 34). This ensures that the attenuation is dominated by the capacitance ratio and is therefore independent of frequency.

The calibration circuit 10 operates as follows. A calibration signal $V_{CAL}$ of known amplitude is applied to the calibration circuit 10, the level at the preamplifier output 26 is determined, and a decision is made, based on this level, as to the integrity of the sensor 14 and its wiring 42, 44. Where the sensor 14 and preamplifier 16 are functioning properly, the output of the preamplifier 16 should be an appropriately scaled replica of the transfer function of the preamplifier 16. Implementing the capacitors 32, 34 as part of the monolithic integrated circuit ensures close matching between the capacitors 32, 34 and the preamplifier 16, and any departure from the expected transfer function is a result of interconnect, sensor capacitance, or preamplifier functioning. In the case of shorted sensor leads, the calibration signal $V_{CAL}$ is dropped across the capacitors 32, 34 with no signal appearing at the preamplifier input leads 22, 24, and thus no signal appearing at the amplifier output 26. In the case of an open sensor lead, there would be reduced attenuation of the calibration signal $V_{CAL}$, resulting in a larger than expected output signal $V_{OUT}$ at the amplifier output 26 and/or change in the shape of the transfer function.

Figure 2:
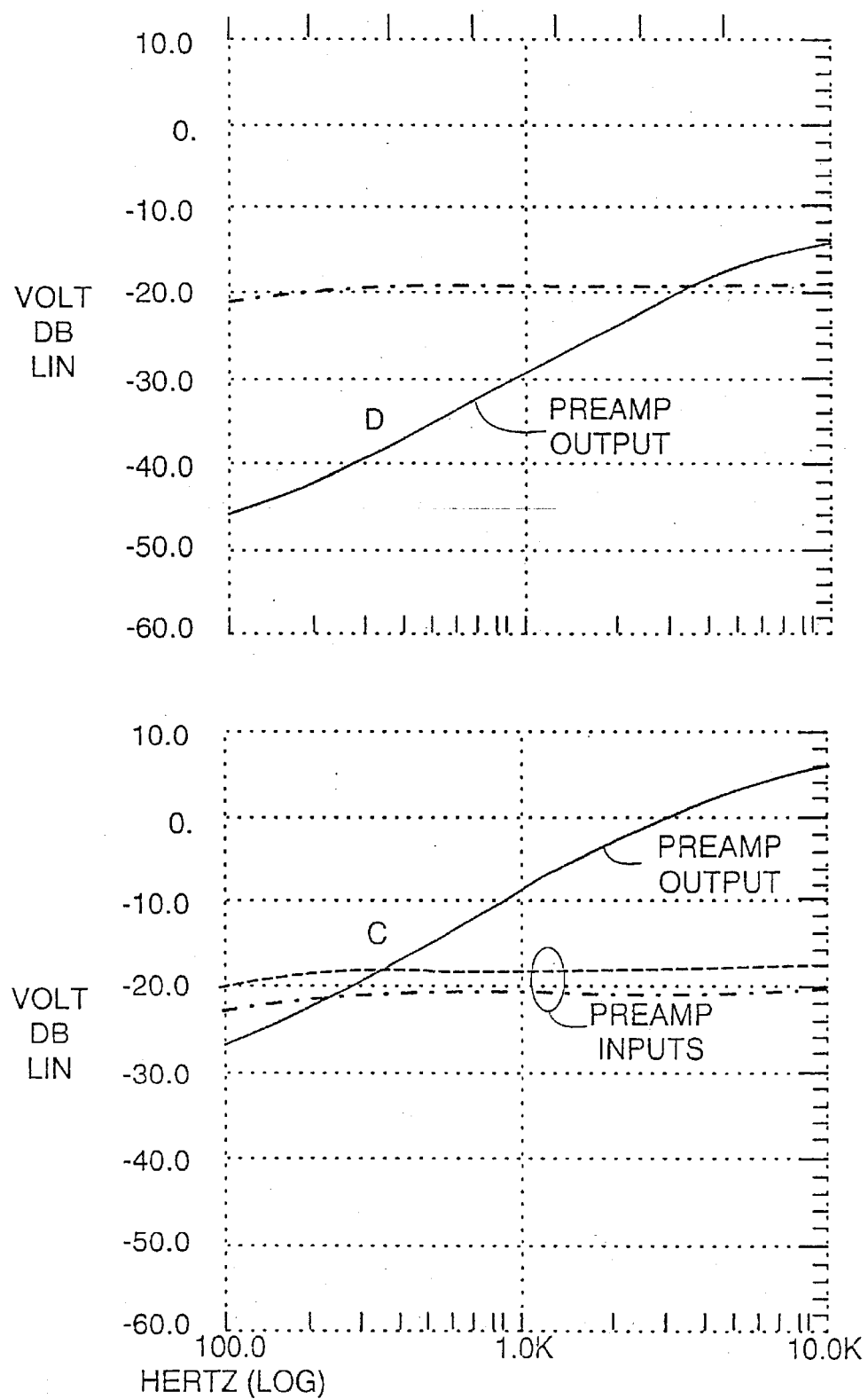
FIG. 2 is a graph depicting gain versus frequency for a simulation of the calibration circuit, according to the present invention.
Figure 3:
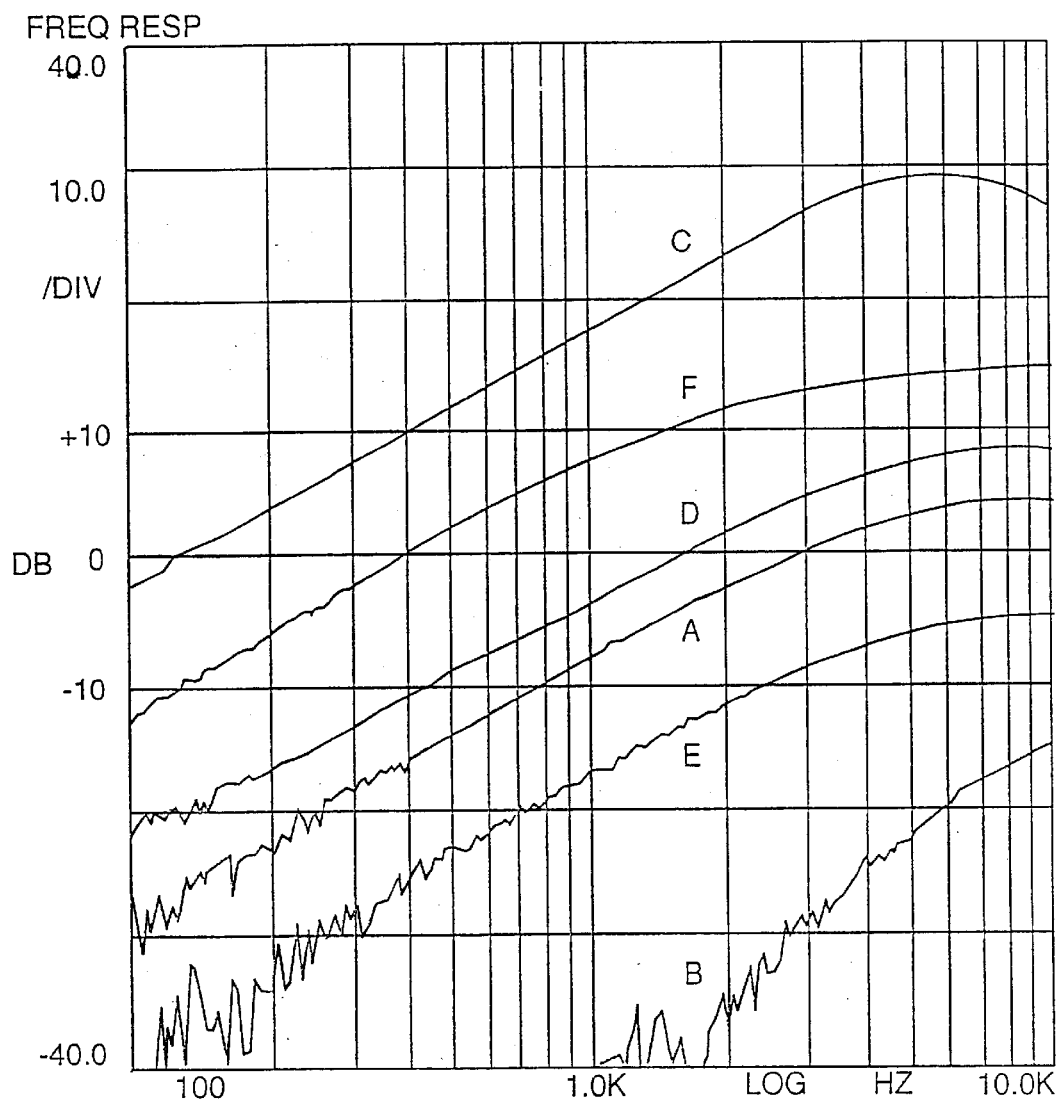
FIG. 3 is a graph depicting gain versus frequency for an operational embodiment of the present invention.

The calibration circuit 10 of the present invention is further described in the context of the test results represented by the graphs in FIGS. 2 and 3. FIG. 2 depicts the results of a computer simulation of a circuit model representing the calibration circuit of the present invention. The curves represent the simulated voltage gain versus frequency. Curve D represents a case of normal operation where the hydrophone capacitance is 60 pF. Curve C represents a case of an open circuit fault where the hydrophone capacitance is 1 pF, which represents remaining parasitics. The 20 dB difference in voltage gain between these two conditions can be recognized by an operator or an automated system to detect when an open circuit fault has occurred in a sensor system.

FIG. 3 depicts the results of measurements using an operational embodiment of the present invention. The curves represent the measured voltage gain versus frequency from the calibration signal input $V_{CAL}$ to the preamplifier output $V_{OUT}$. Similar to the simulation depicted in FIG. 2, curve D represents normal operation for a 56 pF hydrophone capacitance and shows a gain of −4 dB at 1 kHz, and curve C represents an open circuit hydrophone condition and shows a gain of +17 dB. Thus, the difference of 21 dB between these two curves clearly indicates the open circuit condition. Curve B represents a short circuited hydrophone condition and shows a very low gain of the calibration signal.

Curve A represents a 110 pF hydrophone. The difference between curve A and curve D indicates that the calibration circuit is able to differentiate between hydrophones or sensors with different values of capacitance. Curves E and F were measured with one and both preamplifier inputs connected to circuit ground. Although these conditions caused a bias voltage imbalance in the particular preamplifier used for measurement, the fact that a fault condition is present at the hydrophone can still be observed in the preamplifier output 26.

The calibration circuit 10 thus serves at least four different functions. The calibration circuit 10 can be used to detect broken wires 42, 44 between the sensor 14 and the preamplifier 16 and to detect broken wires within the sensor 14. The calibration circuit 10 can be used to detect short circuited wires between the sensor 14 and the preamplifier 16 or within the sensor 14.

Accordingly, the calibration circuit of the present invention indicates the presence or absence of the sensor impedance and exploits the effects of an impedance imbalance, with minimal effects upon the common mode rejection of the amplifier being tested. The minimal size and complexity of the calibration circuit allows it to be easily implemented on the integrated circuit with the preamplifier. The calibration circuit is capable of testing the sensor, interconnect wiring, and transfer function of the preamplifier without requiring substantial external circuitry (except for maybe a calibration voltage source).

In light of the above, it is therefore understood that within the scope of the appended claims, the invention may be practiced otherwise than as specifically described.

What is claimed is:

1. A calibration circuit for a differential input preamplifier having first and second preamplifier input leads, said calibration circuit comprising:

first and second capacitors connected to respective said first and second preamplifier input leads, said first and second capacitors having different capacitance values; and a calibration signal source connected between said first and second capacitors for applying a calibration signal.

2. The calibration circuit of claim 1 wherein said first and second capacitors are implemented on a monolithic integrated circuit with said preamplifier.

3. The calibration circuit of claim 1 wherein said first and second capacitors and said calibration signal source are implemented on a monolithic integrated circuit with said preamplifier.

* * * * *